US011149214B2

(12) United States Patent
Koseoglu et al.

(10) Patent No.: US 11,149,214 B2
(45) Date of Patent: Oct. 19, 2021

(54) METHOD AND PROCESS TO MAXIMIZE DIESEL YIELD

(71) Applicant: Saudi Arabian Oil Company, Dhahran (SA)

(72) Inventors: Omer Refa Koseoglu, Dhahran (SA); Robert Peter Hodgkins, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 16/222,046

(22) Filed: Dec. 17, 2018

(65) Prior Publication Data

US 2020/0190410 A1 Jun. 18, 2020

(51) Int. Cl.
*C10G 57/00* (2006.01)
*C07C 2/68* (2006.01)

(52) U.S. Cl.
CPC .............. *C10G 57/005* (2013.01); *C07C 2/68* (2013.01); *C10G 2300/1048* (2013.01); *C10G 2300/1088* (2013.01); *C10G 2300/1096* (2013.01); *C10G 2300/4006* (2013.01); *C10G 2300/4012* (2013.01); *C10G 2300/42* (2013.01); *C10G 2400/04* (2013.01)

(58) Field of Classification Search
CPC ................ C10G 57/005; C10G 29/205; C10G 2300/1048; C10G 2300/1088; C10G 2300/1096; C10G 2300/4006; C10G 2300/4012; C10G 2300/42; C10G 2300/1044; C10G 2300/104; C10G 2400/04; C07C 2/58; C07C 2/62; C07C 2/66; C07C 2/68
See application file for complete search history.

(56) References Cited

U.S. PATENT DOCUMENTS

| | | | | | |
|---|---|---|---|---|---|
| 3,851,004 | A | * | 11/1974 | Yang | C07C 15/02 585/467 |
| 4,008,291 | A | * | 2/1977 | Zabransky | B01J 8/0453 585/720 |
| 4,025,577 | A | * | 5/1977 | Siskin | C07C 2/00 585/724 |
| 5,476,983 | A | * | 12/1995 | Yan | B01J 27/32 585/719 |

(Continued)

FOREIGN PATENT DOCUMENTS

| | | |
|---|---|---|
| EP | 2631282 A1 | 8/2013 |
| WO | 00/39253 A1 | 6/2000 |

(Continued)

OTHER PUBLICATIONS

Sakuneka et al., Synthetic Jet Fuel Production by Combined Propene Oligomerization and Aromatic Alkylation Over Solid Phosporic Acid, Ind. Eng. Chem. Res. (2008), 7 pages.

(Continued)

*Primary Examiner* — Michelle Stein
(74) *Attorney, Agent, or Firm* — Abelman, Frayne & Schwab

(57) ABSTRACT

Hydrocarbon feeds suitable for use as gasoline blending components containing olefins and aromatic compounds are alkylated in the presence of a catalyst by the olefins present in the feedstream to produce middle distillates having higher boiling points suitable for use as aviation and diesel fuel blending components.

21 Claims, 6 Drawing Sheets

(56) References Cited

U.S. PATENT DOCUMENTS

| | | | |
|---|---|---|---|
| 5,491,270 A | 2/1996 | Chin et al. | |
| 5,675,048 A * | 10/1997 | Zhang | B01J 8/28 |
| | | | 585/467 |
| 7,776,207 B2 | 8/2010 | Abhari et al. | |
| 2004/0158113 A1 * | 8/2004 | Srinivas | C07C 2/58 |
| | | | 585/721 |
| 2006/0144761 A1 * | 7/2006 | Keckler | C07D 333/08 |
| | | | 208/208 R |
| 2011/0147263 A1 | 6/2011 | Umansky et al. | |
| 2011/0240519 A1 * | 10/2011 | Jan | C10G 69/123 |
| | | | 208/70 |
| 2012/0088948 A1 * | 4/2012 | Mukherjee | C10G 57/005 |
| | | | 585/722 |
| 2013/0037446 A1 | 2/2013 | Minoux et al. | |
| 2017/0007993 A1 * | 1/2017 | Timken | C10G 50/00 |

FOREIGN PATENT DOCUMENTS

| | | | |
|---|---|---|---|
| WO | 2000/039253 A1 | 7/2000 | |
| WO | WO-03078360 A1 * | 9/2003 | C07C 2/58 |

OTHER PUBLICATIONS

Quann et al., Chemistry of Olefin Oligomerization Over ZSM-5 Catalyst, Ind. Eng. Chem. Res. (1988), 6 pages.

International Search Report and Written Opinion dated Feb. 19, 2020 in counterpart International Application PCT/US2019/063813 filed Nov. 28, 2019.

\* cited by examiner

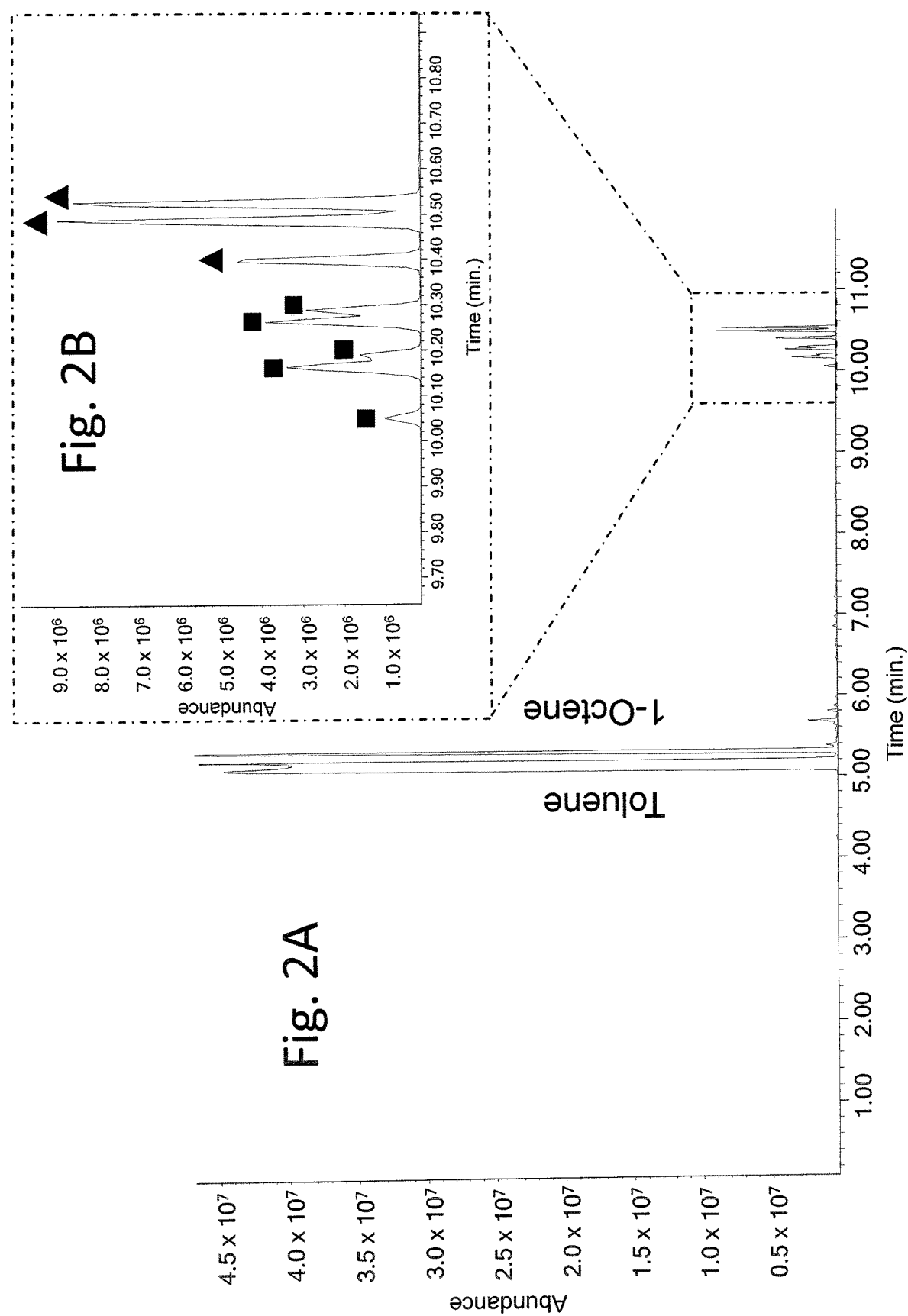

METHOD AND PROCESS TO MAXIMIZE DIESEL YIELD

BACKGROUND OF THE INVENTION

Field of the Invention

The present invention is directed to an integrated refinery process for the production of middle distillates for diesel and aviation fuels, and related blending components.

Description of Related Art

Middle distillates, including commercial transportation fuels and heating oils for residential, commercial and industrial buildings, make up approximately 30 percent of the global market for refined products. The demand for middle distillates has steadily increased worldwide and continues to grow at a higher rate than the demand for any other refined petroleum product.

In the United States, middle distillates serve as the primary fuel source for the transportation of goods throughout the country and are therefore vital to the development of the country's economic infrastructure. Even though gasoline has dominated the United States as the principal passenger-vehicle fuel, diesel fuel has been the primary driver of recent growth in the petroleum markets. Prior to the economic downturn from 2007 to 2009, the demand for diesel fuel in the United States was growing by more than 2 percent annually, compared to demand for gasoline at a growth of 1.2 percent annually. Currently, diesel is expected to once again resume its role as the primary energy source supporting economic expansion and development.

Advancements in diesel refining technology introduced in 2007 resulted in the production of clean ultra-low, i.e., <10 ppmw, sulfur diesel fuel. These advancements have also reduced the emissions of particulate matter and nitrogen oxides by more than 98 percent in heavy duty truck applications when compared to emissions of the early 2000's. Moreover, the technology has resulted in the development and introduction of high performance diesel cars, trucks, and SUVs that are cleaner and quieter than previous models, further increasing the demand for diesel fuel.

The introduction of new fuel economy mandates puts diesel fuel in a position to assume an even greater role in the United States' transportation market. To address rising consumer demand for diesel fuel, retailers have increased availability. In fact, diesel fuel is now available at more than half of all United States retail fuel filling stations. In the near future, refineries will likely be forced to either invest in conversion processes that increase the proportional yield of middle distillates or find alternative processes to produce the middle distillates required to meet the anticipated demand.

With the increasing demand for middle distillates, many new refineries choose hydrocracking over fluid catalytic cracking (FCC) as the primary process for the conversion of the feed to diesel fuel. This is because the hydrocracking process produces a higher diesel yield and superior diesel quality as compared to FCC processes. Additionally, many refineries are utilizing heavy end technologies such as hydroprocessing and coking to convert short or long hydrocarbon residues into transportation fuels.

FCC units produce a significant quantity of high-sulfur, low-cetane number aromatic distillates, e.g., light cycle oil (LCO). Under modern-day diesel quality specifications, this LCO requires deep hydrotreating, hydrogenation, hydrocracking or any combination thereof to produce a diesel- and gasoline-blending component that meets regulatory standards. There are currently a number of high-pressure hydrotreating units that are specifically designed to upgrade LCO produced in FCC processes to a diesel fuel that meets current standards. In addition to reducing sulfur content, these high-pressure hydrotreating units substantially improve the cetane number of the resulting product stream, e.g., with an increase of from 20 to 30 points.

Furthermore, an alternative method for producing high-quality synthetic diesel fuel is to increase the FCC cracking severity to maximize the production of lower molecular weight olefinic products in the gasoline range from the FCC unit and oligomerizing these olefins.

The production of middle distillate blending components from gasoline is well-known in the prior art. For example, WO 2012/076758 discloses a method for producing middle distillate fuel components from gasoline fuel component fractions by the dimerization and/or oligomerization of olefins with carbon numbers ranging from 5 to 7.

Oligomerization reactions yield products that are composed of repetitively linked groups of one or more species of atoms or groups of atoms. Catalysts used to oligomerize olefins include acid catalysts such as zeolites, non-zeolitic acid catalysts, nickel catalysts, and transition metal catalysts. Oligomerization reactions are typically performed at temperatures above 200° C. and at pressures above 50 bar. In the method disclosed in WO 2012/076758, middle distillate hydrocarbons were produced by the oligomerization/polymerization and fractionation of linear aliphatic $C_9$-$C_{16}$ hydrocarbons corresponding to a normal boiling point of approximately 165° C. to 290° C.

The fluoride ion affinity serves as a suitable measure of the strength of a Lewis acid. Christie et al., *J. Fluorine Chem.*, 101 (2000) 151-153, incorporated herein by reference, proposed using a pF$^-$ scale for indicating the strength of Lewis acids.

The alkylation of low carbon number olefins to produce alkylated gasoline blending components is also well known in the prior art. There are numerous alkylation units installed in refineries throughout the world. The most common and widely used alkylation process utilizes a liquid acid, e.g., HF or $H_2SO_4$. Other known processes use super acids, ones with an acidity equal to or stronger than 100% sulfuric acid. Another way to define super acids are those acids with a Hammett acidity value of at least (−12) or lower. For comparison, pure sulfuric acid has a Hammett acidity value of (−12).

Other process modifications to increase middle distillate production have been proposed including lowering the FCC naphtha endpoint.

As a result of the growing demand for middle distillate products, the problem faced by petroleum refiners and addressed by the present disclosure is how to selectively increase the production of middle distillate fuel components from existing feedstocks efficiently and economically to meet this demand.

SUMMARY OF THE INVENTION

The problem of how to selectively increase the production of middle distillate fuel components is addressed by the process of the present disclosure in which hydrocarbon compositions suitable for use as gasoline blending components are catalytically alkylated to middle distillates that include components suitable for use as aviation and diesel fuels. Aromatic compounds are alkylated in the presence of a catalyst by olefins already present in the feedstream to produce middle distillates including diesel blending components. In an embodiment, an olefinic naphtha feedstream having carbon numbers ranging from 5 to 14 is reacted with aromatics compounds in the presence of a catalyst to produce alkylated aromatics, thereby increasing the boiling points of the respective fuel components.

The feedstock can be derived from a unit operation such as an FCC unit, a delayed coking unit, a fluid coking unit, a visbreaking unit, a conventional thermal cracking unit, a pyrolysis unit, a stream cracking unit, or combinations thereof.

The process for upgrading a refinery feedstock comprising a complex mixture derived from a single hydrocarbon cracking unit operation that is rich in C5 to C14 olefins and aromatics boiling in the range of from 15° C. to 250° C. comprises:

a. introducing a feedstock comprising aromatic and olefinic compounds suitable for use as gasoline blending components in an alkylation unit containing at least one catalyst having Lewis and/or BrIInsted acid activity to produce an alkylated product stream having a higher boiling range;

b. recovering the alkylated product stream from the alkylation unit; and c. separating middle distillates from the alkylated product stream.

The terms "naphtha" and "gasoline" as used herein refer to hydrocarbons boiling in the range of from about 36° C. to 180° C. Naphtha is an unprocessed cut while gasoline is a final product.

The term "middle distillate" as used herein refers to hydrocarbons boiling in the kerosene and diesel ranges, generally in the range of from about 140° C. to 370° C.

The term "kerosene" as used herein refers to hydrocarbons boiling in the range of from about 140° C. to 240° C.

The term "diesel" as used herein refers to hydrocarbons boiling in the range of from about 180° C. to 370° C.

BRIEF DESCRIPTION OF THE DRAWINGS

The process of this disclosure will be described in more detail below and with reference to the attached drawings in which:

FIG. 2A is a reproduction or representation of the relevant portion of the graphic plot of the spectra showing the GS-MS reaction products resulting from the alkylation of toluene by 1-octene;

FIG. 2B is an enlarged region of the graphic plot of the spectra of FIG. 2A showing the GS-MS reaction products for the alkylation of toluene by 1-octene;

In the interests of clarity, the simplified schematic illustrations and descriptions do not include the numerous valves, pumps, temperature sensors, electronic controllers and the like that are customarily employed in refinery operations and that are well known to those of ordinary skill in the art.

DETAILED DESCRIPTION OF THE INVENTION

Figure 1:
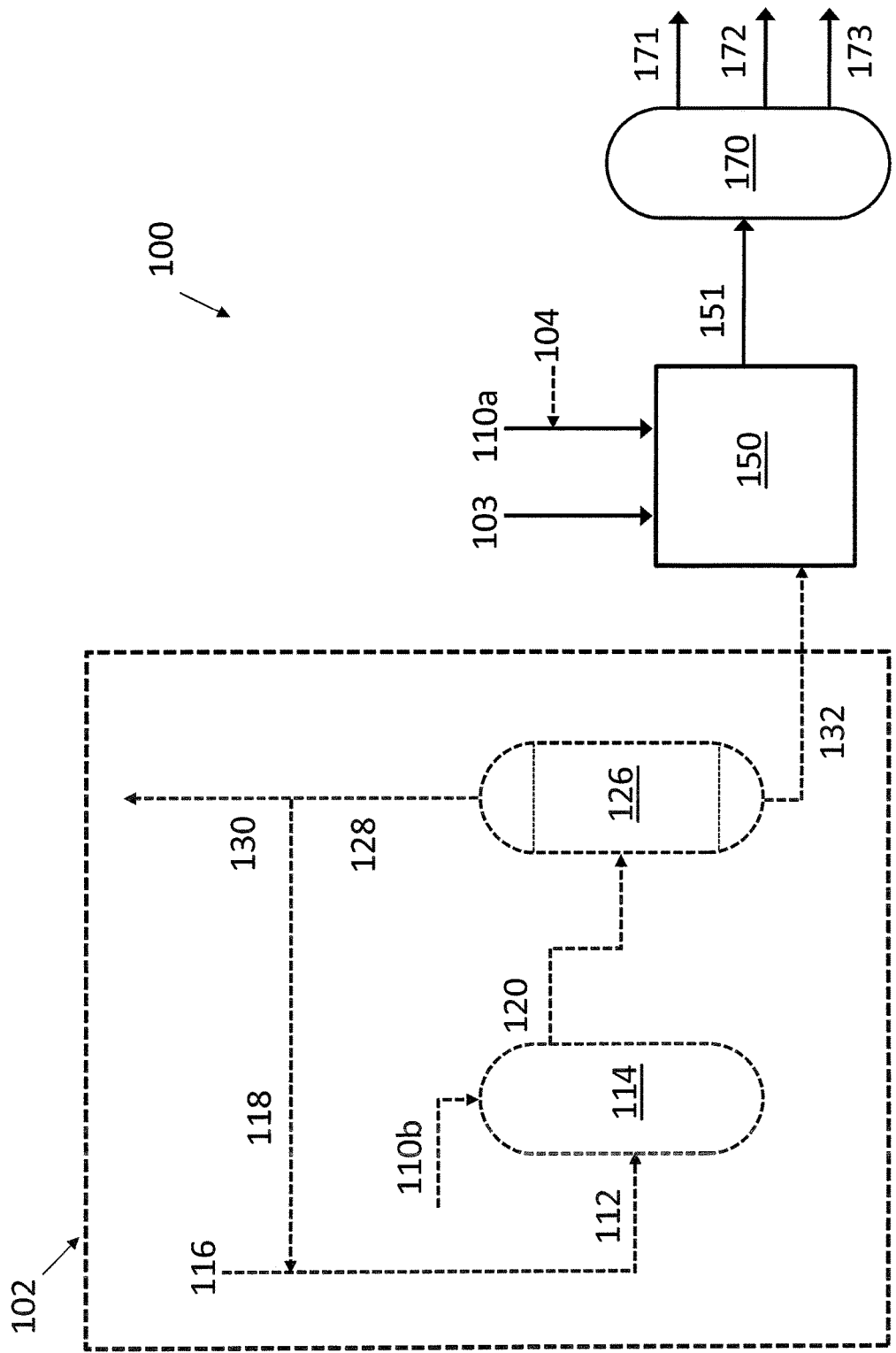
FIG. 1 is a simplified process flow diagram of an integrated alkylation process in accordance with this disclosure.

Referring to FIG. 1, an embodiment of the process of the present disclosure will be described for increasing middle distillate production from an olefinic heavy naphtha stream containing aromatics and olefins with carbon numbers in the range of from 5 to 14 by the catalytic conversion to alkyl aromatics in the diesel boiling point range. The integrated alkylation process and system for its practice is referred to generally as 100. Feedstream 110a enters alkylation unit 150 where it contacts a catalyst 103 for a time that is sufficient to complete the alkylation of the aromatic compounds by the ionic constituents that formed from the dissociation of the olefinic compounds present in the mixed feedstream. An alkylated product stream 151 is recovered and passed to a fractionation zone 170 where gasoline and middle distillates are separated and recovered as product streams 171 and 172, respectively, and a bottoms stream 173 is discharged from the fractionation zone 170.

The fractionation zone 170 can include fractionation units such as flash vessels, fractionation columns, gas stripping, steam stripping, vapor-liquid separators, distillation columns, or a combination of these units.

In an alternative embodiment, hydrogen is mixed with the hydrocarbon feedstream, preferably to the saturation level, to provide a hydrogen-enriched liquid hydrocarbon feed stream. The presence of hydrogen in the feed stream enhances the hydrogen transfer reactions and increases catalyst stability. The hydrogen-to-oil mole ratio is in the range of from 0.05:1 to 1:1, and in preferred embodiments, the hydrogen-to-oil mole ratio is in the range of from 0.05:1 to 0.5:1.

When hydrogen is added to the system, the process can be operated either as a three-phase system i.e., feedstock, excess hydrogen gas and solid catalyst, or it can be a two-phase system in which all of the hydrogen present is dissolved in the liquid feedstock and catalyst. Whether the system is two- or three-phases will depend upon the operating pressure of the system and other reaction conditions that are within the skill of the art.

When hydrogen is present in the system, it functions to prevent or minimize coke formation and thereby maintain the activity of the catalyst. Hydrogen can be consumed to hydrogenate the olefins, but such consumption will be limited to the hydrogen available in the system, and to thermodynamic conditions. There will also be hydrogen losses due to solubility. Hydrogen will therefore not be consumed in substantial quantities. In some embodiments, the amount of hydrogen consumed will be in the range of from 0.01 to 0.1 W % of the $H_2$ in the fresh feedstock.

As shown in FIG. 1, an excess molar quantity of hydrogen 104 is mixed with the feedstream 110a upstream of the alkylation unit 150.

In the two-phase system, all or a substantial portion of the hydrogen required to enhance the hydrogen transfer in the alkylation reactions is dissolved in the liquid feedstock upstream of the alkylation unit in a hydrogen mixing zone. In one embodiment, a hydrogen distribution vessel upstream of the alkylation unit receives hydrogen, fresh feedstock and, optionally, recycled product that has passed through the alkylation reactor, and the liquid is saturated under predetermined conditions of pressure and temperature to dissolve at least a substantial portion of the desired hydrogen gas into the liquid feedstock to produce a combined liquid feed/dissolved hydrogen stream as the feedstock for the alkylation unit. The combined liquid feed/dissolved hydrogen stream preferably is a hydrogen saturated feedstock, also referred to as a hydrogen-enriched feedstock.

Gas phase hydrogen is eliminated or substantially reduced by flashing the feedstock containing the dissolved hydrogen under predetermined conditions upstream of the alkylation unit to produce a single reactant phase of liquid hydrocarbon feedstock containing dissolved hydrogen, preferably at the saturation level under the prevailing operating conditions of temperature and pressure of the alkylation unit 150. The alkylation unit will then operate as a two-phase system, i.e., the liquid hydrocarbon feed with dissolved hydrogen and one or more small particle size solid heterogeneous catalysts.

This optional two-phase hydrogen addition embodiment employs a hydrogen distribution vessel 102 that includes a mixing/distribution zone 114 that is alternatively referred to herein as the mixing zone, having at least one inlet for receiving a liquid hydrocarbon feedstock stream 110b and at least one inlet for receiving a hydrogen gas stream 112 or, alternatively, a combined inlet for receiving both the feedstock and hydrogen gas, and an outlet for discharging a combined stream 120 of hydrogen enriched feedstock and excess hydrogen.

The flashing zone 126 has an inlet in fluid communication with the outlet discharging a combined stream 120, a gas outlet 128 in fluid communication with one or more hydrogen gas inlets of the mixing/distribution zone 114, and an outlet (132) for discharging hydrogen-enriched feedstock. In this embodiment, the hydrogen-enriched feedstock is sent to alkylation unit 150.

In the operation of the hydrogen distribution vessel 102, a liquid hydrocarbon feedstock stream 110b is intimately mixed with the hydrogen gas stream 112 in the mixing/distribution zone 114 to dissolve a predetermined quantity of hydrogen gas in the liquid mixture to produce a hydrogen-enriched liquid hydrocarbon feedstock and an excess of hydrogen gas. The incoming hydrogen gas stream 112 includes a fresh hydrogen stream 116 and a recycled hydrogen stream 118 from the flashing zone 126. The stream 120 is conveyed to the flashing zone, or flashing vessel 126 in which the undissolved hydrogen and any other gases present, e.g., light feedstock fractions, are flashed off and removed as a flash stream 128.

The flashing zone 126 can include one or more flash drums that are operated at suitable pressure and temperature conditions to maintain a predetermined concentration of hydrogen in solution in the liquid hydrocarbon when it is passed to the downstream alkylation unit 150 which is operated under predetermined conditions of temperature and pressure.

A portion 118 of the recycled hydrogen stream 128 is recycled and mixed with the fresh hydrogen feed 116. The amount of recycled hydrogen in the hydrogen gas stream 112 generally depends upon a number of factors relating to the amount of excess undissolved hydrogen that is recovered from the flashing zone 126. The remaining portion of the flashed gases are discharged from the system as a bleed stream 130.

The mixing/distribution zone 114 described in FIG. 1 can be any apparatus that achieves the necessary intimate mixing of the liquid and gas so that hydrogen is dissolved in the liquid hydrocarbon feedstock under predetermined conditions to achieve the desired degree of alkylation in accordance with the reaction mechanism. In other embodiments, the mixing zone can include a combined inlet for the hydrogen and the feedstock. Effective unit operations include one or more gas-liquid distribution vessels, which apparatus can include spargers, injection nozzles, or other devices that impart sufficient velocity to inject the hydrogen gas into the liquid hydrocarbon with turbulent mixing and thereby promote hydrogen saturation.

The hydrogen-enriched hydrocarbon feedstock stream 132 containing a predetermined quantity of dissolved hydrogen, preferably at the saturation level, is combined with catalyst 103 in the alkylation unit 150.

The feed streams 110a or 110b are derived from any suitable unit operation that is conveniently available within the battery limits of the refinery. For example, the source of the feedstream can be an FCC unit, a thermal cracking unit, or a combination thereof. The types of thermal cracking unit operations from which suitable olefin streams are derived are delayed or fluid coking units, visbreaking units, conventional thermal cracking units, pyrolysis units, steam cracking units, and other cracking processes that do not employ hydrogen. As will be apparent to one of ordinary skill in the art, not all of these unit operations are likely to be found within a single refinery.

In certain embodiments, the olefins concentration in the feed can range from 1 W % to 60 W %. In preferred embodiments, the W % of the olefins concentration in the feed is in the range of from 30-46, 30-59, 30-9, 39-46, 39-59, 39-9, 6-46, 6-59 or, 6-9 W %. In certain embodiments, the aromatic concentration in the feed is in the range of from 1 W % to 60 W %. In preferred embodiments, the aromatic W % of the concentration in the feed is in the range of from 13-19, 13-16, 13-37, 10-19, 10-16, 10-37, 25-19, 25-16, or 25-37 W %.

A suitable catalyst for use in the process is a soluble homogeneous compound or a heterogeneous compound selected from resins, amorphous or structured metal oxides, metal fluorides, metal chlorides having Lewis acid and/or BrIInsted acid sites. The metals in the catalysts are selected from Periodic Table IUPAC Groups 4-12 based on characteristics known to those of ordinary skill in the art or determined by routine experimentation.

In certain embodiments, a suitable catalyst for use in the process is an amorphous silica alumina catalyst or a zeolite catalyst. The zeolites can be selected from AFI-, ATS-, Beta-, CON-, EMT-, EUO-, FAU-, FER-, IFR-, ITQ-, MFI-, MOR-, MSE-, MTW-, MWW-, NES-, NFI-, STF-, MCM-, and ZSM-based zeolites. Preferred zeolites include the FAU-, MOR-, Beta-, MFI-, and MCM-based zeolites.

In some embodiments, strong acids are preferred, such as those possessing a high $pF^-$ value, for example those having a $pF^-$ value greater than 1.0.

In preferred embodiments, heterogeneous catalysts are used that have both Lewis acidity and BrIInsted acidity. A combination of catalysts with similar functionalities, i.e., alkylation catalysts, are present in the alkylation unit.

In certain embodiments, suitable catalysts for the present process include Lewis acids disclosed in Christie et al. having a $pF^-$ value of greater than 1. Those acids include $SbF_5$, $AlF_3$, $AlFCl_2$, $AlF_2Cl$, $AlCl_3$, $TeOF_4$, $InF_3$, $GaF_3$, $AsF_3$, $SnF_5$, $SnF_4$, $Cis-IO_2F_3$, $PF_5$, $SeOF_4$, $TeF_4$, $BF_3$, $GeF_4$, $ClF_5$, $BrF_3$, $SiF_4$, $SeF_4$, $SOF_4$, $XeOF_4$, $TeF_6$, $POF_3$, $XeF_4$, $SF_4$, $COF_2$, $PF_3$, $HF$, $NO_2F$ and $NOF$.

In some embodiments, the alkylation reaction can be conducted at a temperature in the range of from about 25° C. to less than 250° C. In preferred embodiments, the alkylation reaction is conducted at a temperature in the range of from about 25° C. to 90° C. In certain embodiments, the alkylation reaction is conducted at a pressure in the range of from about 1 bar to 30 bar.

In all embodiments, the alkylated product stream 151 has a higher boiling temperature range than the initial feedstreams 110a or 110b.

As previously noted, additional equipment such as pumps, compressors, separation vessels, and the like that are known to those skilled in the art have not been shown in the interests of clarity.

Example 1: Alkylation of Toluene by 1-Octene

Six reactions were carried out using an AlCl$_3$ catalyst at various catalyst-to-oil and toluene-to-1-octene ratios. All the reactions were conducted at a temperature of 90° C. and atmospheric pressure that was maintained for 4 hours. Table 1 summarizes the run parameters.

TABLE 1

| RUN No. | Catalyst | Catalyst g | Toluene g | 1-Octene g | Feedstock g | Cat-to-oil ratio g/Kg |
|---|---|---|---|---|---|---|
| 1 | AlCl$_3$ | 0.212 | 80.6 | 4.9 | 85.6 | 2.5 |
| 2 | AlCl$_3$ | 0.198 | 78.9 | 6.4 | 85.3 | 2.3 |
| 3 | AlCl$_3$ | 0.266 | 66.9 | 16.3 | 83.2 | 3.2 |
| 4 | AlCl$_3$ | 0.201 | 54.5 | 26.5 | 81.1 | 2.5 |
| 5 | AlCl$_3$ | 0.152 | 75.5 | 9.2 | 84.7 | 1.8 |
| 6 | AlCl$_3$ | 0.101 | 75.5 | 9.2 | 84.7 | 1.2 |

Referring to FIG. 2A, the resultant GC-MS spectrum is depicted for the alkylation of toluene by 1-octene corresponding to Run No. 1 of Table 1. FIG. 2B depicts an enlarged region of the alkylated products and eight different structural/stereo isomers are clearly shown. The isomers have an empirical formula of C$_{15}$H$_{24}$, where the alkyl group, with different structural or stereo isomers, are identified on the toluene ring. These spectra clearly indicate that the alkylation of toluene by 1-octene was achieved.

FIG. 2A shows that toluene and 1-octene elute at relatively shorter retention times, i.e., at 5-6 minutes, whereas the heavier products of alkylation elute over longer retention times, i.e., at 10-10.6 minutes.

Figures 2C, 2D:
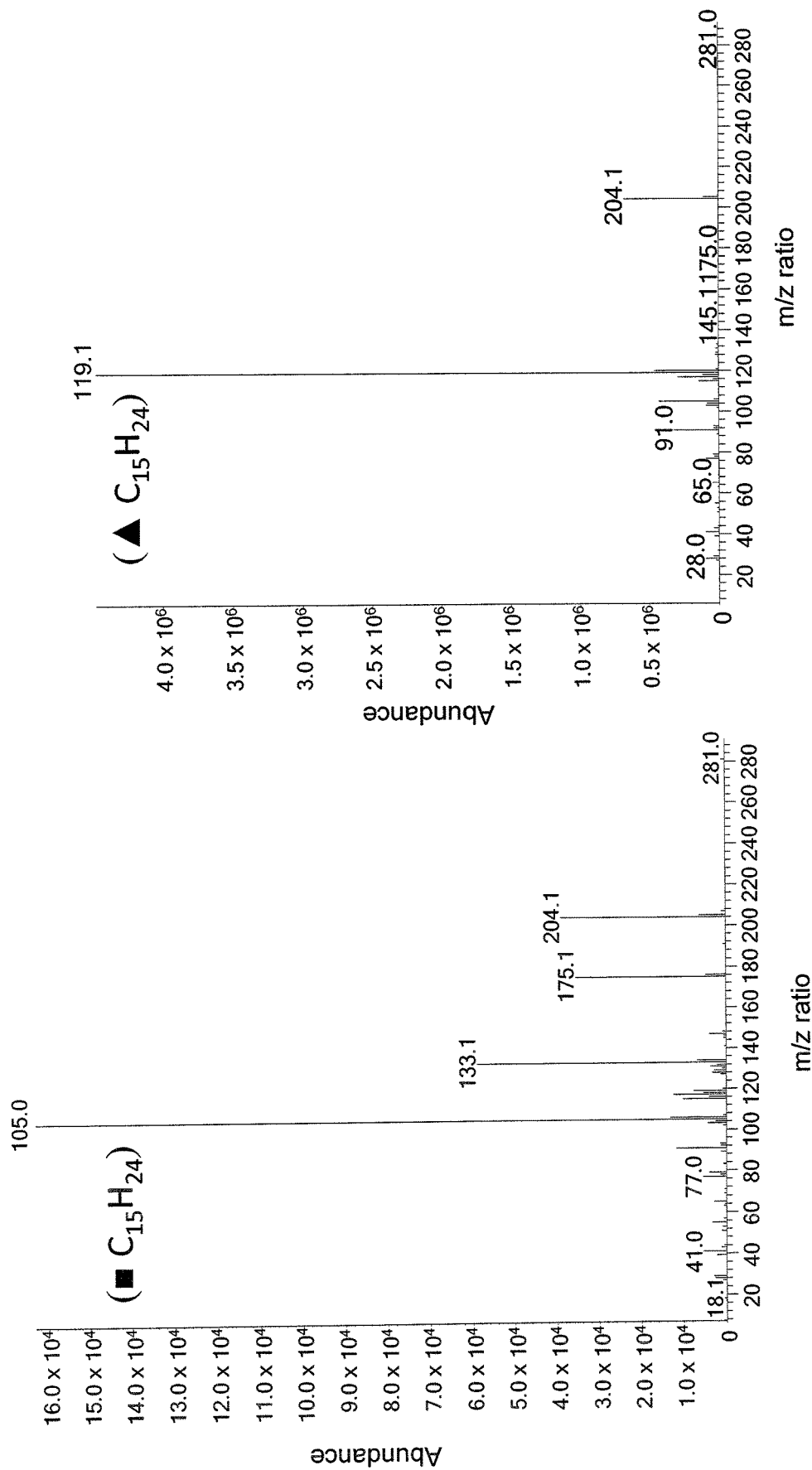
FIG. 2C is a reproduction of the mass spectrum for certain isomers of $C_{15}H_{24}$.
FIG. 2D is a reproduction of the mass spectrum for certain isomers of $C_{15}H_{24}$.

FIG. 2C shows the mass spectrum for peaks in FIG. 2B identified by a square. The mass spectrum indicates features consistent with methylated (m/z 105) benzene species.

FIG. 2D shows the mass spectrum for peaks in FIG. 2B identified by a triangle. The mass spectrum indicates features consistent with dimethylated (m/z 119) benzene species.

For comparison, the alkylation of toluene by 1-octene using USY-5 as the catalyst was undertaken in a manner similar to that of AlCl$_3$. USY-5 is a Y-type zeolite having a silica-to-alumina molar ratio of 5. No reaction was apparent in any of the runs using USY-5 as the catalyst.

Example 2

Aromatic alkylation runs were carried out using a feedstock of FCC naphtha without any pretreatment. The properties of the FCC naphtha are set out in Table 2. The feedstream compositionally contained 17.7 W % boiling above 180° C.

TABLE 2

| Property | Unit | Value |
|---|---|---|
| Density @15° C. | g/cc | 0.7615 |
| API gravity | ° | 54.3 |
| Nitrogen | ppmw | 14 |
| Sulfur | ppmw | 4,000 |
| n-Paraffins | W % | 4.4 |
| i-Paraffins | W % | 25.0 |
| Olefins | W % | 26.7 |
| Naphthenes | W % | 9.1 |
| Aromatics | W % | 33.0 |
| Other components | W % | 1.8 |
| Initial Boiling Point (IBP) | ° C. | 15 |
| BP at 5 W % | ° C. | 24 |
| BP at 10 W % | ° C. | 29 |
| BP at 30 W % | ° C. | 72 |
| BP at 50 W % | ° C. | 107 |
| BP at 70 W % | ° C. | 153 |
| BP at 90 W % | ° C. | 201 |
| BP at 95 W % | ° C. | 221 |
| Final Boiling Point | ° C. | 270 |

The following set of reactions employed four different catalysts. The first catalyst is AlCl$_3$, as discussed above a known Lewis acid catalyst.

The second catalyst is ZEO1, a zeolite-based catalyst with no active phase metals, designed to crack heavy oils at high temperatures and low pressures.

The third catalyst is ZEO2E, a zeolite-based catalyst in extrudate form containing Ni and Mo as active phase metals, designed for use in hydrocracking processes.

The fourth catalyst is ZEO2P, a zeolite-based catalyst in powder form containing Ni and Mo as active phase metals, designed for use in hydrocracking processes.

Both the ZEO2E and ZEO2P have a 4 wt % nickel oxide and a 16 wt % molybdenum oxide loaded onto the catalyst.

Additionally, ZEO1, ZEO2E and ZEO2P zeolites comprise SiO$_2$ and Al$_2$O$_3$ with a portion of the Al$_2$O$_3$ being substituted for TiO$_2$ and ZrO$_2$, i.e., their framework is modified.

A number of reactions were conducted for each catalyst by varying the catalyst-to-oil weight ratios. Table 3 summarizes the matrix of reaction conditions. The mass of the catalyst has been normalized to the zeolite content.

TABLE 3

| RUN No. | Catalyst | Cat Type | C/O Ratio, g/Kg |
|---|---|---|---|
| 1-6 | AlCl$_3$ | Powder | 6.7-65.7 |
| 7-12 | *ZEO1 | Powder | 2.0-19.7 |
| 13-17 | *ZEO2E | Extrudate | 6.5-52.4 |
| 18 | No Catalyst | | — |
| 19-24 | *ZEO2E | Extrudate | 6.7-65.7 |

The GC-MS analyses revealed that the FCC naphtha feed was successfully alkylated using the AlCl$_3$ catalyst.

Figure 3:
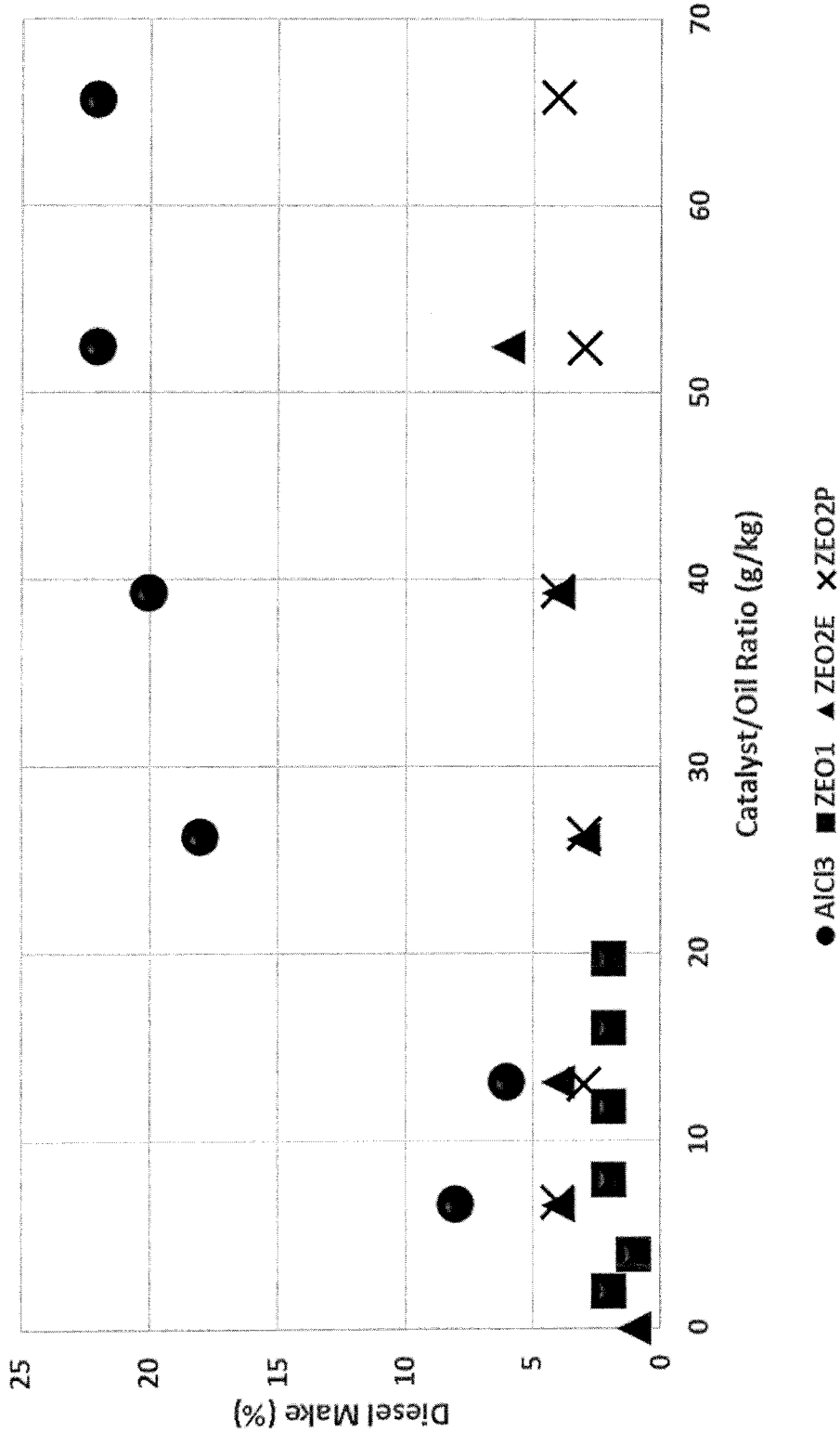
FIG. 3 is a graph illustrating the production of diesel blending components as a function of the catalyst-to-oil weight ratio employed in the process of the present disclosure.

The conversion of naphtha to diesel blending components increases with an increasing catalyst-to-oil ratio. FIG. 3 shows the production of diesel as a function of catalyst-to-oil ratio. For example, a 22 V % increase in production of diesel was observed at a catalyst-to-oil ratio of 65.7 g/kg with AlCl$_3$ as the catalyst. This value represents the increase in the amount of the components boiling in the diesel range as compared to the feed.

Figure 4:
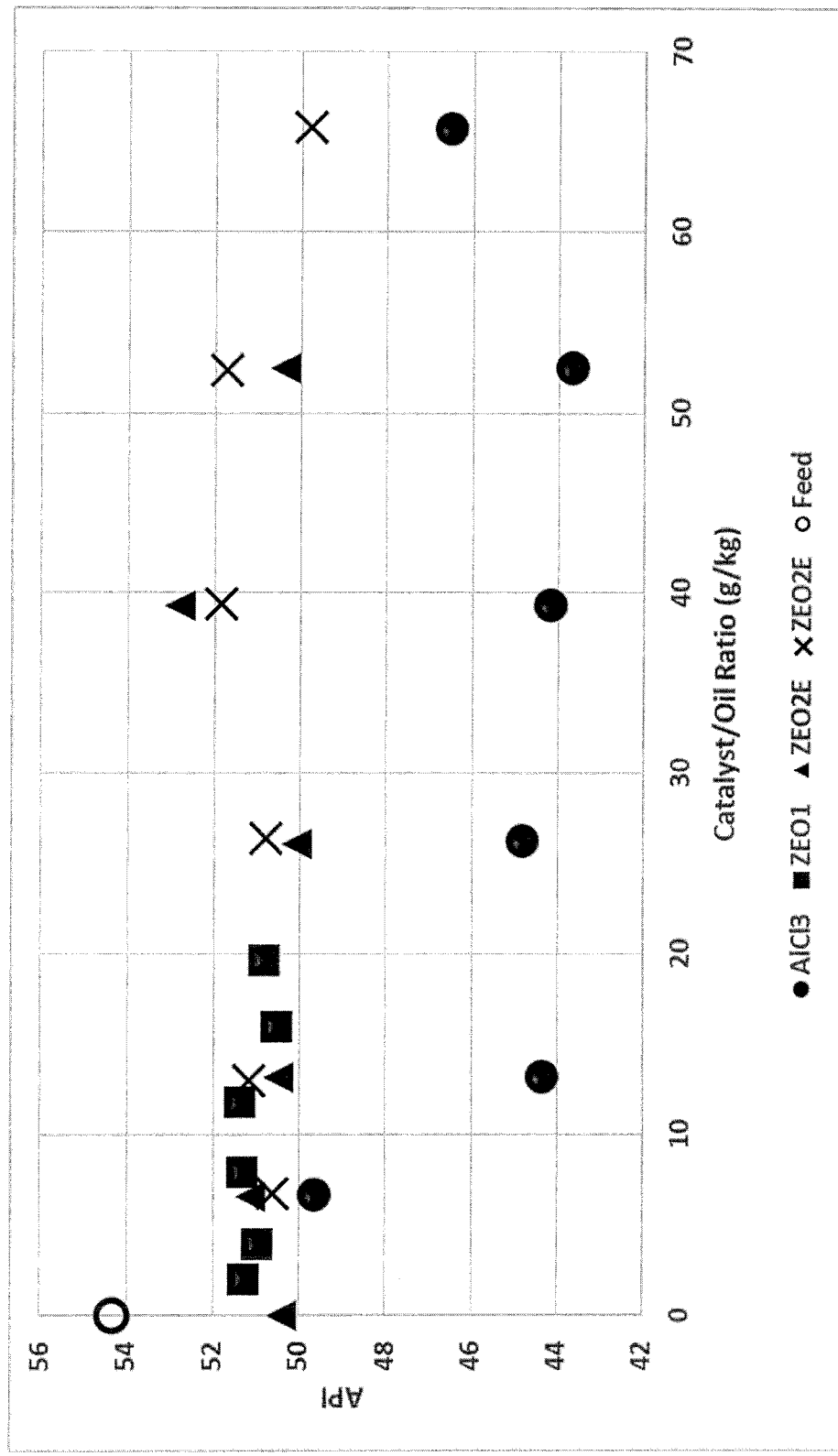
FIG. 4 is a graph illustrating the API gravity of the total liquid products as a function of the catalyst-to-oil ratio employed in the process of the present disclosure.

As a result of the increase in molecular weight with alkylation, the API gravity of the total of the liquid products decreased. The variation in the API gravity of liquid products as a function of catalyst-to-oil ratio is shown in FIG. 4.

As shown in Table 2, the feedstream had an API gravity of 54.3°. When the $AlCl_3$ catalyst-to-oil ratio was 52.3, the API gravity decreased to 43.6°, constituting a decrease in the API gravity of 10.7 degrees. Based on this data, $AlCl_3$ appears to be the most active catalyst under the specified constant reaction conditions.

The above results demonstrate that the alkylation of aromatics by olefins present in cracked naphtha shifted the boiling points of hydrocarbons from the naphtha range into the middle distillate range. Hydrocarbons boiling in the naphtha range were converted into hydrocarbons boiling in the middle distillate range that are useful as diesel blending components.

Figure 5:
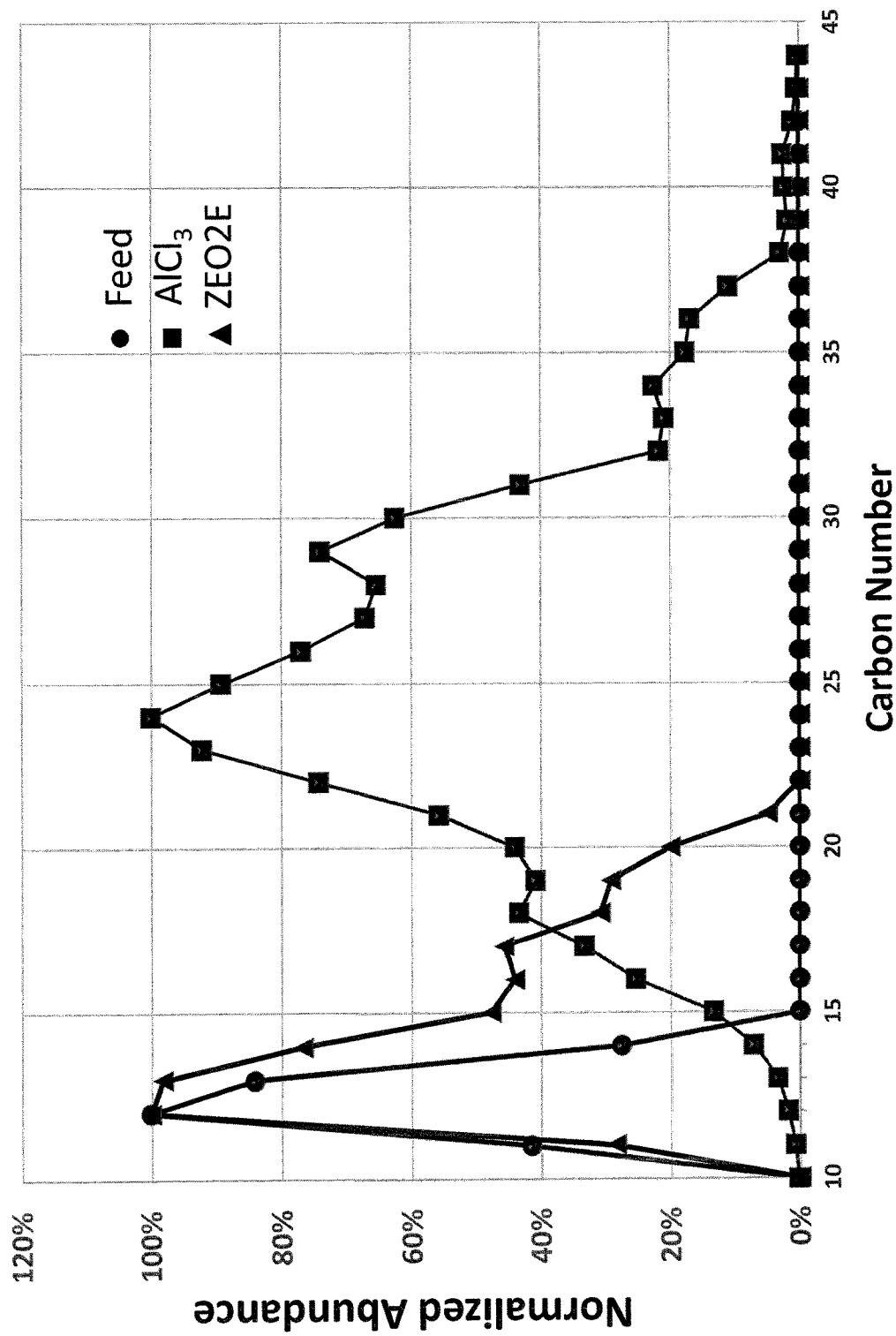
FIG. 5 is a graph illustrating the carbon number of the feed and selected products produced in accordance with the process of the present disclosure.

Referring to FIG. 5, the carbon number relative abundance for runs using $AlCl_3$ and ZEO2E as a catalyst, with catalyst-to-oil ratios of 65.7 and 52.4, respectively, are shown, and an increase in carbon number occurs with both catalysts. $AlCl_3$ appears from this data to be the most active catalyst under the specified constant reaction conditions.

The method and system of the present invention have been described above and in the attached drawings, and modifications will be apparent to those of ordinary skill in the art and the scope of protection for the invention is to be determined with reference to the claims that follow.

The invention claimed is:

1. A process for upgrading a refinery feedstock derived from one or more hydrocarbon cracking operations that is a complex mixture rich in $C_5$ to $C_{14}$ olefinic compounds and aromatic compounds boiling in the range of from 15° C. to 250° C., the process comprising:
   a. introducing the feedstock and excess hydrogen gas into a hydrogen mixing zone to produce a liquid hydrocarbon feedstock containing dissolved hydrogen and excess hydrogen gas;
   b. flashing the liquid hydrocarbon feedstock containing dissolved hydrogen in a flashing zone to separate a single-phase reactant of liquid hydrocarbon feedstock containing dissolved hydrogen from a stream of excess hydrogen;
   c. introducing the single-phase reactant of liquid hydrocarbon feedstock containing dissolved hydrogen recovered from the flashing zone into an alkylation unit in the presence of at least one catalyst having Lewis acid and/or Brønsted acid activity;
   d. maintaining the olefins and aromatics in contact with the catalyst in the alkylation unit for a time and under predetermined conditions so that substantially all of the aromatic compounds in the original feedstock are alkylated by the olefinic compounds in the original feedstock to produce an alkylated product having a higher boiling temperature range,
      whereby the alkylation occurs as a two-phase reaction;
   e. recovering an alkylated product stream from the alkylation unit;
   f. passing the alkylated product stream to a fractionation zone to separate middle distillates from the alkylated product stream; and
   g. recovering a middle distillate product stream.

2. The process of claim 1, wherein the catalyst is a heterogeneous Lewis acid catalyst.

3. The process of claim 2, wherein the catalyst is selected from the group consisting of resins, amorphous metal oxides, structured metal oxides, metal fluorides, metal chlorides, $SbF_5$, $AlF_3$, $AlFCl_2$, $AlF_2Cl$, $AlCl_3$, $TeOF_4$, $InF_3$, $GaF_3$, $AsF_3$, $SnF_5$, $SnF_4$, $Cis-IO_2F_3$, $PF_5$, $SeOF_4$, $TeF_4$, $BF_3$, $GeF_4$, $ClF_5$, $BrF_3$, $SiF_4$, $SeF_4$, $SOF_4$, $XeOF_4$, $TeF_6$, $POF_3$, $XeF_4$, $SF_4$, $COF_2$, $PF_3$, $HF$, $NO_2F$, $NOF$, and combinations thereof.

4. The process of claim 3, wherein the catalyst comprises an amorphous silica alumina catalyst or a zeolite catalyst.

5. The process of claim 3, wherein the metal oxide comprises a metal from groups 4-12 of the Periodic Table.

6. The process of claim 1, wherein the catalyst is a homogeneous metal catalyst or a homogeneous organometal catalyst having Lewis acidity.

7. The process of claim 6, wherein the metal catalyst or organometal catalyst comprises a metal selected from Groups 4-12 of the Periodic Table.

8. The process of claim 1, wherein the catalyst is a heterogeneous catalyst having Brønsted acidity.

9. The process of claim 8, wherein the catalyst is a resin, an amorphous metal oxide or a structured metal oxide.

10. The process of claim 9, wherein the catalyst is an amorphous silica alumina catalyst, a titania catalyst or a zeolite catalyst.

11. The process of claim 9, wherein the metal oxide comprises a metal selected from groups 4-12 of the Periodic Table.

12. The process of claim 1, wherein the catalyst comprises a homogeneous metal catalyst or an organometal catalyst having Brønsted acidity.

13. The process of claim 12, wherein the metal catalyst and the organometal catalyst comprise a metal selected from groups 4-12 of the Periodic Table.

14. The process of claim 1, wherein the catalyst has a $pF^-$ value of greater than or equal to 1 or a Hammett acidity value of at least (−12).

15. The process of claim 1, wherein the fractionation zone includes one or more flash vessels, fractionation columns, gas stripping units, steam stripping units, vapor-liquid separators, distillation columns, and combinations thereof.

16. The process of claim 1, wherein the alkylation takes place at a hydrogen-to-oil mole ratio in the range of from 0.05:1 to 0.5:1.

17. The process of claim 1, wherein the alkylation reaction is conducted at a temperature in the range of from 25° C. to less than 250° C.

18. The process of claim 1, wherein the alkylation reaction is conducted at a temperature in the range of from 25° C. to 90° C.

19. The process of claim 1, wherein the alkylation reaction is conducted at a pressure in the range of from 1 bar to 30 bar.

20. The process of claim 1, wherein the feedstock is derived from a unit operation selected from the group consisting of an FCC unit, a delayed coking unit, a fluid coking unit, a visbreaking unit, a conventional thermal cracking unit, a pyrolysis unit, a stream cracking unit, and combinations thereof.

21. The process of claim 1, wherein the feedstock recovered from the flashing zone is saturated with hydrogen.

* * * * *